(12) United States Patent
Escalier et al.

(10) Patent No.: US 10,881,289 B2
(45) Date of Patent: Jan. 5, 2021

(54) DEVICE FOR TESTING THE VISUAL BEHAVIOR OF A PERSON, AND METHOD FOR DETERMINING AT LEAST ONE OPTICAL DESIGN PARAMETER OF AN OPHTHALMIC LENS USING SUCH A DEVICE

(71) Applicant: Essilor International, Charenton-le-Pont (FR)

(72) Inventors: Guilhem Escalier, Charenton-le-Pont (FR); Isabelle Poulain, Charenton-le-Pont (FR); Benjamin Rousseau, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 90 days.

(21) Appl. No.: 15/768,382

(22) PCT Filed: Oct. 14, 2016

(86) PCT No.: PCT/FR2016/052665
§ 371 (c)(1),
(2) Date: Apr. 13, 2018

(87) PCT Pub. No.: WO2017/064441
PCT Pub. Date: Apr. 20, 2017

(65) Prior Publication Data
US 2018/0310820 A1 Nov. 1, 2018

(30) Foreign Application Priority Data

Oct. 15, 2015 (FR) .................................... 15 59812

(51) Int. Cl.
*A61B 3/02* (2006.01)
*A61B 3/11* (2006.01)
(Continued)

(52) U.S. Cl.
CPC .......... *A61B 3/0091* (2013.01); *A61B 3/0041* (2013.01); *A61B 3/024* (2013.01);
(Continued)

(58) Field of Classification Search
CPC ..... A61B 3/113; A61B 3/0025; A61B 3/0091; A61B 3/145; A61B 3/032; A61B 3/152;
(Continued)

(56) References Cited

U.S. PATENT DOCUMENTS 6,367,932 B1 4/2002 Donaldson
7,950,800 B2 5/2011 Nauche et al.
(Continued)

FOREIGN PATENT DOCUMENTS

FR 2 914 173 A1 10/2008
FR 3 012 952 A1 5/2015
(Continued)

OTHER PUBLICATIONS

International Search Report dated Feb. 7, 2017, in PCT/FR2016/052665, filed Oct. 14, 2016.
(Continued)

*Primary Examiner* — Brandi N Thomas
(74) *Attorney, Agent, or Firm* — Oblon, McClelland, Maier & Neustadt, L.L.P.

(57) ABSTRACT

A device for testing visual behavior of a person, including: an active display configured to display at least one visually predominant target in a plurality of positions that are variable over time and that are aligned along at least one line or column, and a unit for controlling the display. The unit is programmed so that consecutive display positions of the target follow, over time, a visual tracking protocol.

21 Claims, 6 Drawing Sheets

(51) Int. Cl.

| | |
|---|---|
| *A61B 3/00* | (2006.01) |
| *A61B 3/113* | (2006.01) |
| *G02C 7/02* | (2006.01) |
| *G02C 13/00* | (2006.01) |
| *A61B 3/032* | (2006.01) |
| *A61B 3/024* | (2006.01) |
| *A61B 3/14* | (2006.01) |

(52) U.S. Cl.
CPC .............. *A61B 3/032* (2013.01); *A61B 3/113* (2013.01); *A61B 3/145* (2013.01); *G02C 7/025* (2013.01); *G02C 13/005* (2013.01)

(58) Field of Classification Search
CPC ....... A61B 5/162; A61B 5/163; A61B 3/0058; A61B 3/0083; A61B 3/08; A61B 3/14; A61B 3/15; A61B 3/154; A61B 3/0041; A61B 3/005; A61B 5/0484; A61B 5/11; A61B 5/4088; A61B 3/0033; A61B 3/024; A61B 3/028; A61B 3/102
USPC .................................. 351/221–224, 243–246
See application file for complete search history.

(56) References Cited

U.S. PATENT DOCUMENTS

| | | | |
|---|---|---|---|
| 8,231,220 B2 | 7/2012 | Baranton | |
| 8,360,580 B2 | 1/2013 | Chauveau | |
| 2010/0060850 A1* | 3/2010 | Giraudet | G02C 7/021 |
| | | | 351/159.59 |
| 2010/0195051 A1 | 8/2010 | Murray et al. | |
| 2013/0314668 A1 | 11/2013 | Haddadi et al. | |
| 2014/0171756 A1 | 6/2014 | Waldorf et al. | |
| 2015/0051508 A1* | 2/2015 | Ghajar | A61B 5/163 |
| | | | 600/558 |

FOREIGN PATENT DOCUMENTS

| | | |
|---|---|---|
| JP | 2010-46327 | 3/2010 |
| JP | 2015-79127 | 4/2015 |
| WO | WO 99/22638 A1 | 5/1999 |
| WO | WO 2008/139137 A1 | 11/2008 |

OTHER PUBLICATIONS

Office Action dated Sep. 2, 2020 in Japan Patent Application No. 2018-519277 (with English translation), 6 pgs.

* cited by examiner

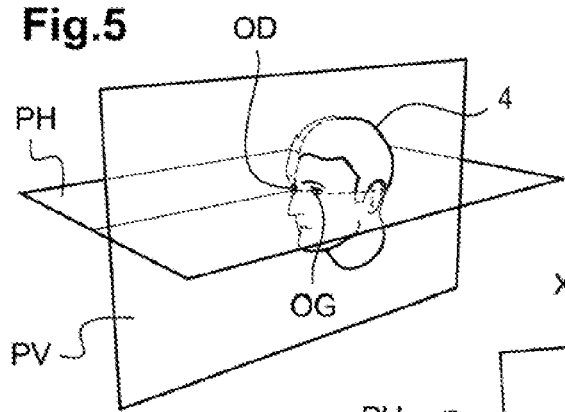
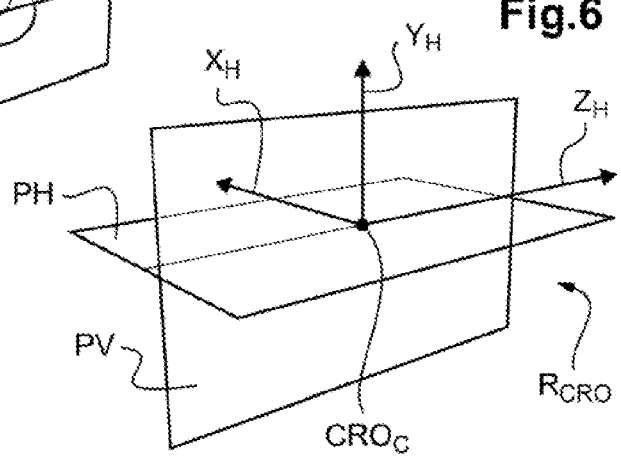
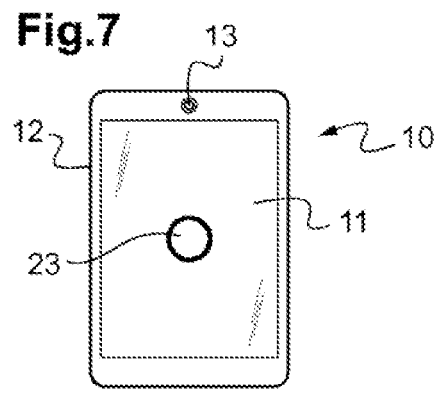
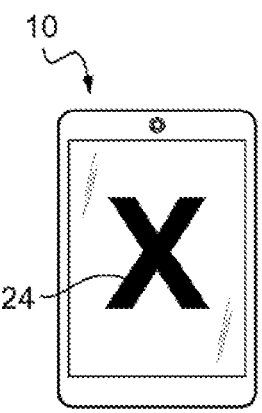 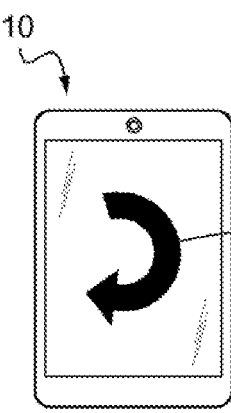 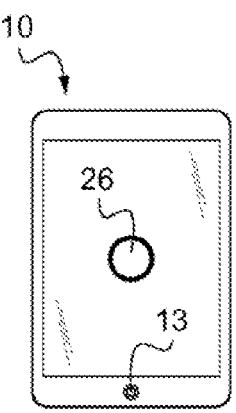

DEVICE FOR TESTING THE VISUAL BEHAVIOR OF A PERSON, AND METHOD FOR DETERMINING AT LEAST ONE OPTICAL DESIGN PARAMETER OF AN OPHTHALMIC LENS USING SUCH A DEVICE

TECHNICAL FIELD OF THE INVENTION

The present invention generally relates to a testing device allowing the visual behavior of an individual to be determined.

It also relates to a method for determining at least one optical parameter for designing an ophthalmic lens using such a device.

TECHNOLOGICAL BACKGROUND

The ever more precise personalization of ophthalmic lenses for a frame with which an individual is intended to be equipped in order to correct his vision requires increased knowledge of the visual behavior of the individual under vision conditions that are natural and representative of the actual use of said ophthalmic lenses.

Determining parameters of the visual behavior of the individual then allows the optical design of the ophthalmic lenses that will be mounted in the frame to be improved.

In particular, during the optical design of progressive ophthalmic lenses, it is particularly important to have at one's disposition pertinent optical design data in order to take into account how these lenses are used in near vision and the posture adopted by the individual, in particular when reading.

However, the measurements currently carried out by an optician on an individual are most often constrained, in particular because the individual is not able to wear a vision-correcting means or because the measuring apparatus or vision-testing devices used cause the individual to adopt a posture that is unnatural, in particular for near-vision activities.

The same goes when the individual is wearing a vision-correcting means that, in addition, may no longer be suitable for his refraction. In this case, the measurements are corrupted, since the prismatic effect of the correction of the optical power of the means affects the posture of the individual.

In addition, it is difficult to get an individual with poor sight to adopt a natural reading posture unless he is wearing his vision-correcting means, individuals suffering from myopia tending to decrease their reading distance and those suffering from presbyopia tending to increase this distance.

Conversely, measurements then taken while the individual is performing a visual task other than reading are then taken under unnatural conditions and therefore do not represent the way in which a progressive lens would be used day-to-day.

Vision-testing devices are therefore inaccurate and the optical design parameters determined by the optician are therefore not always representative of the visual behavior of the individual under natural conditions.

As a result, the optical design of progressive lenses is not optimal and hence it may be difficult to tailor progressive ophthalmic lenses to the wearer.

SUBJECT OF THE INVENTION

In order to remedy the aforementioned drawbacks of the prior art, the present invention proposes a device for testing the visual behavior of an individual allowing the visual behavior of an individual to be determined in a simple and precise manner.

More particularly, according to the invention a device is proposed for testing the visual behavior of an individual, this device including:
- an active display suitable for displaying at least one visually predominant target in a plurality of positions that vary over time and that are aligned in at least one row or one column, and
- a unit for controlling the display, this unit being programmed so that the successively displayed positions of the target follow, over time, a visual tracking protocol.

Thus, by virtue of the device according to the invention, it is possible to test the visual behavior of the individual in a reading situation under natural conditions. Said target may be tracked by the gaze of any individual, whether an adult or child, literate or not, and independently of the language spoken by the individual. In addition, the target may be tracked by the gaze of an individual even when he is not wearing an article of vision-correcting equipment.

Provision may in particular be made for all the successively displayed positions to be such that the target remains in the visual field of the individual. In other words, the individual is able to track the target throughout the eye test.

Thus, there is no risk of a target, whether visually predominant or not, not being detected by the testing device.

On the contrary, the testing device is designed to make the individual look in quite particular directions in his visual field, and in no case outside thereof, as this would run the risk of introducing the risk of measurement errors.

By virtue of the device according to the invention, an accurate visual behavior parameter of the individual may be determined.

According to one particularly advantageous feature of the invention, said positions of the target are aligned in at least two rows or two columns that are substantially parallel.

Also advantageously, said plurality of positions comprises, in each row or column, at least three aligned positions of said target.

The following are other nonlimiting and advantageous features of the method according to the invention, which may be implemented individually or in any technically possible combination:
- the controlling unit to makes it so that, in each position of said visual tracking protocol, the target is displayed for a predetermined duration.
- said predetermined duration is comprised between 50 milliseconds and 1 second;
- said target remains stationary for said predetermined duration;
- the controlling unit makes it so that there is a predetermined lag between the display of the target in two successive positions of the visual tracking protocol;
- said predetermined lag varies over the course of the visual tracking protocol;
- said target is invisible during said predetermined lag;
- said target is visible during said predetermined lag and moves between the two corresponding successive positions of the visual tracking protocol, from one to the other;
- said controlling unit makes it so that two successive positions of the visual tracking protocol are separated by a distance smaller than 10 centimeters;

said controlling unit makes it so that two successive positions of the visual tracking protocol are separated by a distance that varies throughout the visual tracking protocol;

said controlling unit stores a favored vertical direction of travel and favored horizontal direction of travel of the visual tracking protocol in memory;

the display of said target in two successive positions of the visual tracking protocol follows said preferred direction of travel at least six times in ten;

said substantially parallel rows along which the predetermined positions of the target are aligned extending substantially horizontally, the direction of travel of the visual tracking protocol is identical for all the successive rows, from the highest to the lowest, i.e. from right to left or left to right;

said substantially parallel rows along which the predetermined positions of the target are aligned extending substantially vertically, the direction of travel of the visual tracking protocol is identical, i.e. from the top to bottom or bottom to top, for all the successive rows from left to right or right to left;

the controlling unit is programmed to allow said visual tracking protocol to be selected from a plurality of visual tracking protocols recorded in a local or remote database in which a direction of travel is recorded in association with the visual tracking protocol to which it corresponds;

the visual tracking protocol follows a reading trajectory which accords with that defined by a given writing system, so as to reproduce the displacement of the gaze of the individual while reading in accordance with the writing system.

The invention also proposes a method for determining at least one optical parameter for designing an ophthalmic lens intended to be mounted in a frame chosen by an individual, depending on the visual behavior of the latter.

According to the invention, this method uses the aforementioned testing device and comprises the following steps:

a) the individual is asked to perform a visual task in which he looks at the target displayed by said display of the display device, the positions of said target being predetermined in a frame of reference attached to an image-capturing apparatus, b) images of the head of the individual looking at said target are captured by means of said image-capturing apparatus, each image corresponding to a predetermined position of said target, c) on the basis of at least some of the images of the head of the individual, positions of the head of the individual in a frame of reference attached to said image-capturing apparatus or gaze directions of the individual in a frame of reference attached to the head of the individual are determined, each position of the head or gaze direction of the individual being associated with the position of said target for which the corresponding image of the head of the individual was captured, d) said sought-after optical design parameter is deduced from said cephalic positions or gaze direction of the individual.

The method according to the invention allows an optical design parameter that is representative of the visual behavior of the individual to be determined.

Using this method to determine the optical design parameter thus allows the vision zones of the ophthalmic lens to be better tailored to the characteristics of the individual.

According to one particularly advantageous feature of the invention, prior to step d), the positions of said target are re-expressed, on the basis of said determined positions of the head or the gaze directions of the individual, in a frame of reference attached to the head of the individual, and, in step d), said sought-after optical design parameter is deduced from said positions of the target in the frame of reference attached to the head of the individual.

DETAILED DESCRIPTION OF AN EXEMPLARY EMBODIMENT

The description which follows with reference to the appended drawings, which are given by way of nonlimiting examples, will make it easy to understand what the invention consists of and how it may be achieved.

In the appended drawings:

FIG. 5 is a schematic view of the head of the individual;

FIG. 6 shows a frame of reference attached to the head of the individual;

FIGS. 7 to 11 show the testing device of FIG. 1 in various steps of an adjusting phase of the method of the invention;

By way of preamble, it will be noted that identical or similar elements of the various embodiments shown in the various figures will be referenced by the same reference signs and will not be described each time.

It will also be noted that in the disclosure which will follow, the terms "top" (or "upper") and "bottom" (or "lower") will be used in relation to the individual using the test device, top designating the side turned towards the head of the individual and bottom designating the side turned towards the feet of the individual.

Likewise, the term "front" will designate the side turned towards the individual, the term "rear" designating the side opposite to the front side.

Figure 1:
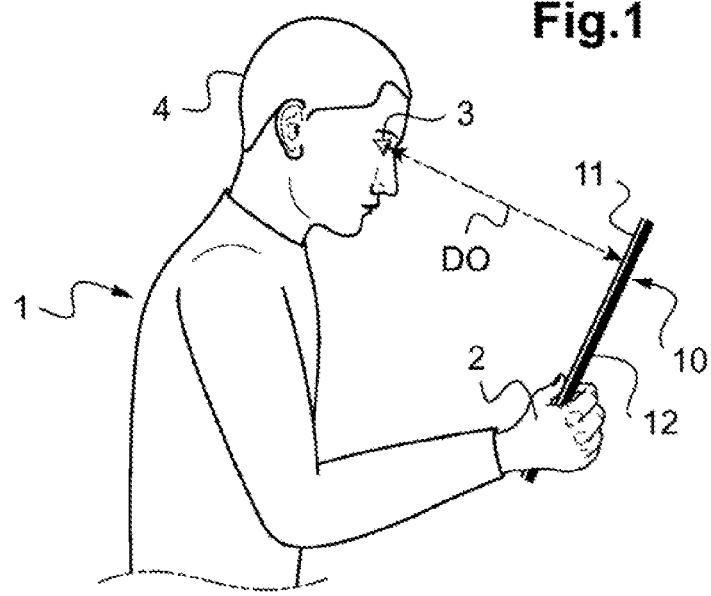
FIG. 1 is a schematic view of an individual holding in his hands a testing device in accordance with the invention.

FIG. 1 shows an individual 1 whose visual behavior it is desired to test.

For this purpose, the individual 1 holds in his hands 2 a testing device 10 in accordance with the invention intended to determine this visual behavior under given conditions.

More particularly here, it is desired to use the testing device 10 to analyze in a general manner the near vision of the individual 1, and in particular the visual behavior that he adopts when he is in a reading situation.

It will be considered that near vision corresponds to an observation distance DO (see FIG. 1) between the eye 3 of the individual 1 and the testing device 10 of smaller than 70 centimeters (cm).

In other embodiments, intermediate vision (DO lying between 70 cm and 4 meters) or far vision (DO larger than 4 m) may be tested by virtue of the testing device according to the invention.

According to the invention, the testing device 10 includes (see FIG. 2):

- an active display 11 that displays a visually predominant target 20 at a plurality of positions 30 that vary over time and that are aligned in at least one row or column; and
- a unit (not shown) for controlling the display 11, which unit is programmed so that the successively displayed positions 30 of the target 20 follow, over time, a visual tracking protocol, in which all the successively displayed positions are such that the target remains in the visual field of the individual.

The display 11 of the testing device may display, at each instant of the eye test, one single target or indeed a plurality of targets simultaneously, each target being in the visual field of the individual. In both cases, the visually predominant target is a target that is suitable for catching the eye of the individual and that the individual will follow over the course of the eye test.

If said target were not in the visual field of the individual, he would not be able to detect it.

When a plurality of targets are displayed by the display 11 in the visual field of the individual, the visually predominant target may, for example, be a brighter or more contrasted target, of different color or shape (round, square, star-shaped, etc.) or of smaller or larger size than the others, or indeed a target that blinks whereas the others do not. The various targets displayed by the display may also comprise a set of indicators or indeed form a grid of grey dots.

In embodiments in which the display displays only one target, the latter may adopt a plurality of positions on the display 11, insofar as the adopted positions remain in the visual field of the individual. These positions "vary" in the sense that the target moves sequentially from one position to another over the course of the eye test. Nevertheless, it will be noted that the sequence of positions successively adopted by the target in these embodiments may comprise two identical positions. In other words, it is possible, during the eye test, for the target to return to a position that it was in before.

In embodiments in which the display displays a plurality of targets one of which is visually predominant, the displayed positions of the targets may vary over time, in the interior of the visual field of the individual, but, in any case, the visually predominant target adopts a sequence of positions in the visual field of the individual so as to make the individual 1 look in a succession of particular gaze directions.

In the present description, "visual tracking protocol" will therefore be understood to mean the sequence in which the visually predominant target 20 is displayed over the course of the eye test carried out by the individual 1, these successively displayed positions being such that the target 20 remains in the visual field of the individual 1.

In other words, this visual tracking protocol corresponds to the succession, over time, of the positions adopted by the visually predominant target. By virtue thereof, a protocol is imposed on the individual who looks successively in a plurality of particular desired directions that are each associated with a particular position adopted by the target. In this way, if the positions of this target are known, it is then possible, under certain conditions, to determine information relating to the gaze direction of the individual during the eye test.

Figure 2:
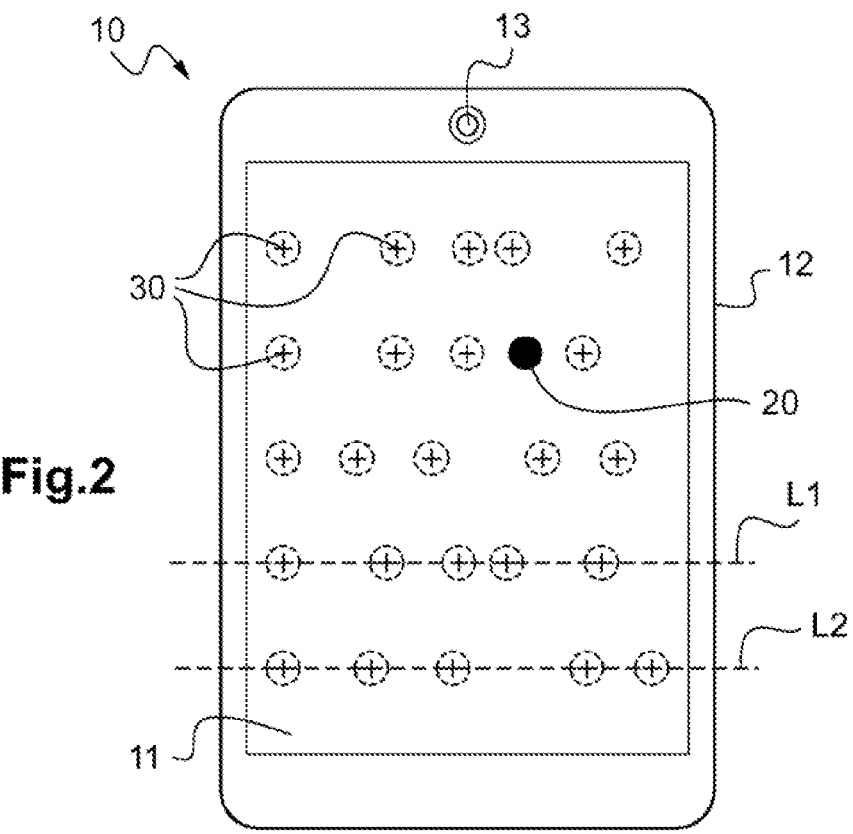
FIG. 2 is a face-on view of the testing device of FIG. 1.

As illustrated in FIG. 2, here the testing device 10 takes the form of a tablet computer. This tablet computer comprises a screen which constitutes the display 11 of the testing device 10. It also comprises a casing 12 encircling the screen and a front video camera 13 that is able to see the individual 1. The controlling unit of the device 10 corresponds, for its part, to the display controller of screen of the tablet, which screen is housed inside the casing 12.

Here the target 20 comprises a luminous disc that is displayed on the screen of the tablet, the size of the target being sufficient for it to be seen by the individual 1 under the conditions of the eye test. Here, under reading conditions and in near vision (DO<70 cm), the target 20 has a characteristic size (e.g. diameter) of larger than 5 millimeters.

Advantageously, the characteristic size of the target 20 is determined in such a way that it may be seen with an acuity of larger than 0.1 tenths at 70 cm.

As a variant, the target may comprise a regular or irregular geometric pattern. It is preferably a question of any pattern except a symbol used by any writing system understood by the individual. In particular, the visually predominant target has no meaning to the individual. For example, the target is not a word that is intelligible to the individual.

Various types of visual tracking protocols that are implemented by the testing device 10 according to the invention and that are intended here to simulate the reading of a text by the individual 1 will now be described with reference to FIG. 4.

Advantageously, the display of the target according to the visual tracking protocols implemented by the testing device 10 acts as a visual stimulus for the individual 1, intended to make him move his eyes by tracking this target 20 according to the same scheme as that which the individual 1 would adopt if he were actually reading a text.

In other words, the display of the visually predominant target on the display is controlled in such a way that, when the individual follows with his gaze the target, the direction of the gaze of the individual exhibits successive gaze directions which are entirely similar to the gaze directions that this individual would have when reading a text.

The sequence of the displayed positions adopted successively by the visually predominant target is preferably predetermined depending on a reference text, and/or on a reading model, corresponding to the characteristics and/or to the reading/writing preferences of the individual.

For example, the sequence may be predetermined previously with another device, in the course of a calibration operation during which the individual is asked to choose a reference text and/or a reading model from among a plurality of available actual texts and to read it aloud. The reading speed may then serve as parameter for determining the display positions of the target.

The sequence may also be predetermined depending on the individual's age or depending on a reading level declared by the individual, subsequent to a questionnaire filled in by the individual.

It is also possible to envisage doing a training run with an average speed, asking the individual if this average speed was too fast or not fast enough and adjusting the speed depending on his response.

It will be observed firstly that the reading of a text by an individual is done naturally according to a reading scheme comprising three distinct operations: fixations, saccades and reverse saccades.

During fixations, the individual deciphers the word that he is in the process of reading, that is to say the word on which the individual's gaze is fixed.

During saccades, corresponding to the displacement phases, that is to say to passing from the reading of one word to the following word, the individual's eyes move rapidly so as to pass from one fixation to another.

These saccades are related to the visual span, that is to say to the number of characters (letters, symbols, ideograms, etc.) which are decipherable for a given fixation. They allow the reader to decipher all the characters of a text.

The saccades generally take place in the direction of reading of the text. Nonetheless, the eyes also perform very fast "reverse saccades" in the direction opposite to the direction of reading so as to pass from one fixation to another. This movement is induced by an error of the oculomotor muscles or by poor reading and understanding of the text.

One of the advantages of the testing device 10 according to the invention is to propose visual tracking protocols which come as close as possible to the individual's reading schemes.

The testing device 10 therefore makes it possible to simulate, simply, the reading of a text and to place the individual in a situation in which he will adopt a natural posture close to that which he would adopt for reading in near vision.

A determination of the visual behavior of the individual under these conditions is therefore rendered more precise and the optical design of an ophthalmic lens intended for the individual may be improved so that the design of the ophthalmic lens meets the needs of the individual in terms of vision correction.

Preferably, the positions of the target 20 are aligned in at least two rows L1, L2 (case of positions 35, 36, 37, 38 and 39 for the row L2 of FIG. 3) that are substantially parallel. More precisely, in the exemplary embodiment shown in the figures, the unit for controlling the display 11 is programmed so that the successively displayed positions 30 of the target 20 are aligned in five rows.

Alternatively, the positions of the target may be aligned in at least two columns.

Generally, the positions of the target 20 may be aligned in parallel lines of any direction, in particular substantially horizontal or vertical for the individual 1.

Figure 3:
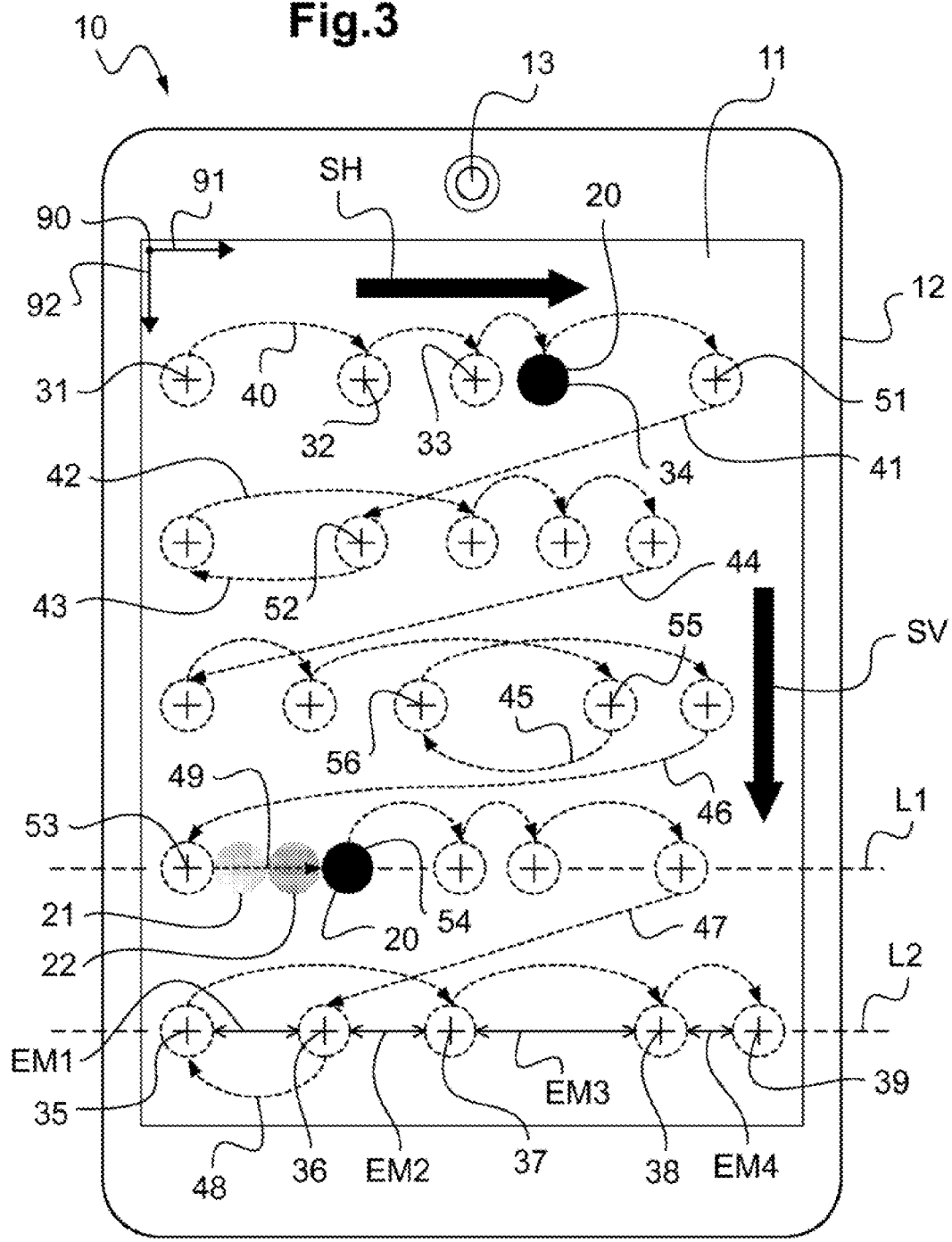
FIG. 3 is a schematic view showing various visual tracking protocols used in the device of FIG. 1.

Preferably again, each row L1, L2, or alternatively each column, comprises at least three aligned positions of said target (case of the positions 35, 36, 37, 38 and 39 for the row L2 of FIG. 3).

In order for the visual tracking protocol to represent the way in which the wearer reads as well as possible, provision will advantageously be made for the visual tracking protocol to describe a reading trajectory that accords with that defined by a given writing system, so as to reproduce the way in which the gaze of the individual moves when he reads in accordance with the writing system.

The reading trajectory may be defined here as the path, on the display 11, scanned by the gaze direction of the individual 1 when he looks at the sequence of positions 30 adopted by the visually predominant target 20.

The reading scheme adopted by an individual is related not only to the nature or to the specific properties of the text, but also to the specific features of each type of writing.

It will be noted moreover that the various types of writing may be classified in a functional manner (alphabetic, syllabic or logographic writing) and a directional manner (horizontal and vertical direction of writing and/or reading).

Provision is therefore made in the testing device for the controlling unit to store in memory a favored vertical SV and horizontal SH direction of travel (see FIG. 3) of the visual tracking protocol.

This favored vertical and horizontal direction of travel is determined beforehand depending on the characteristics of the individual, and in particular his ability to read a text according to a given writing system.

For example, when the testing device is used by a French person who reads from right to left and from top to bottom, the horizontal direction of travel stored by the controlling unit is a direction of travel going from the left of the screen 11 to the right of the screen 11, and the vertical direction of travel stored by the controlling unit is a direction of travel going from the top of the screen 11 to the bottom of the screen 11.

Hence, in one preferred embodiment, the substantially parallel rows L1, L2 along which the positions 35, 36, 37, 38, 39 of the target 20 are aligned extend substantially horizontally, the direction of travel of the visual tracking protocol being identical for all the rows taken successively from the topmost to the bottommost, from left to right (or from right to left for right-to-left writing such as Arabic or Hebrew).

In the same manner, when the testing device is used by a Mongolian, who reads from top to bottom and from right to left, the vertical direction of travel stored by the controlling unit is a direction of travel going from the top of the screen 11 to the bottom of the screen 11, and the horizontal direction of travel stored by the controlling unit is a direction of travel going from the right of the screen 11 to the left of the screen 11.

Hence, in an embodiment suitable for this writing system, the substantially parallel lines along which the predetermined positions of the target are aligned extend substantially vertically, the direction of travel of the visual tracking protocol being identical, from top to bottom or from bottom to top, for all the lines taken successively from right to left.

Advantageously, the controlling unit of the testing device 10 is programmed to allow the visual tracking protocol to be selected from a plurality of visual tracking protocols recorded in a local or remote database, in which a direction of travel is recorded in association with the visual tracking protocol to which it corresponds.

Thus, the individual depending on his own reading and/or writing characteristics may choose the visual protocol which corresponds to him, so that he is under natural reading-like conditions whilst carrying out the eye test. It is then certain that his reading mechanisms and strategies are put in place so as to recover the posture which is most representative of the use of his near vision. In order to reproduce the reading scheme such as described above, with fixations, saccades and reverse saccades, provision is made for the controlling unit of the display 11 to display the target 20 according to a preferential visual tracking protocol.

Hence, provision is made for the controlling unit to make it so that, in each position of the visual tracking protocol, the target 20 is displayed for a predetermined duration. This is intended to mean that the target 20 is kept displayed (case of the position 34 of FIG. 3) fixedly on the screen in such a way that the individual 1 is forced to fixate his gaze on the target 20, this corresponding to a fixation on the reading trajectory of the individual 1.

Advantageously, the target is fixated for the predetermined duration, that is to say that the position of the target 20 for this predetermined duration does not change, before passage to the following position of the reading trajectory.

Preferably, this predetermined duration lies between 50 milliseconds and 1 second, thus corresponding typically to standard fixation times.

The predetermined duration may also vary in the course of the reading trajectory, this accounting for the fact that the fixation of the gaze of the individual 1 on a word during actual reading may depend on the word (size, length) and on the level of understanding (poorly known or unknown word, nearly indecipherable word or character, poorly spelt word, etc.).

Advantageously also, provision is made for the controlling unit to impose a predetermined lag between the displays of the target 20 in two successive positions 31, 32 (see FIG. 2) of the visual tracking protocol.

In this manner, it is possible to simulate by virtue of the testing device 10 the saccades or reverse saccades existing along the reading trajectory of the individual 1. As previously, provision may be made for the controlling unit to vary the predetermined lag in the course of the visual tracking protocol.

This makes it possible to allow for the fact that the reading speed of the individual 1 may vary in the course of the reading of a text.

This also makes it possible to envisage the cases where the gaze direction of the individual passes from one line to another, as is the case for example from the position 51 to the position 52 of FIG. 3, returning to the line requiring more time insofar as the variation of gaze direction of the individual is more significant.

It is then possible to provide two cases for the target during the predetermined lag.

In one embodiment, provision may be made for the target to be invisible during the predetermined lag. This corresponds to the case of the positions 31 and 32 of FIG. 3 in which the target 20 "jumps" (the jump being represented by the dashed arrow 40) from the position 31 to the following position 32. This embodiment makes it possible to allow for the gaze of the individual that jumps from word to word while reading a text.

In an alternative embodiment, provision may be made for the target to be visible during the predetermined lag and to move between the two corresponding successive positions of the visual tracking protocol, from one to the other. This corresponds to the case of positions 53 and 54, the target moving (the movement being represented by the dashed arrow 49), while remaining visible (see targets 21 and 22), from the position 53 corresponding to the first position on the fourth row of the protocol to the position 54 here corresponding to the second position on the fourth row of the protocol. This other embodiment, for its part, allows a word that the gaze of the individual alights on in its entirety before passing to the following during reading to be modeled.

Advantageously, the testing device 10 of the invention is such that the controlling unit makes it so that two successive positions 35, 36, 37, 38, 39 of the visual tracking protocol are separated by a distance EM1, EM2, EM3, EM4 smaller than 10 centimeters. In this manner, during the eye test, there is no need for the individual 1 to vary his gaze direction in a way that would cause him to exert himself, as is generally the case when reading.

Preferentially, provision is moreover made for the controlling unit to make it so that the distance EM1, EM2, EM3, EM4 separating two successive positions 35, 36, 37, 38, 39 of the visual tracking protocol varies throughout the visual tracking protocol. This makes it possible to adapt the separation between the targets 20 displayed depending on the average span of the words for a given writing system.

In another embodiment, the controlling unit is programmed so that the display of the target 20 in two successive positions of the visual tracking protocol follows the favored horizontal and/or vertical direction of travel at least six times out of ten. This is illustrated in FIG. 3 in which directions of travel have been represented in the visual tracking protocol, these directions of travel being represented by the dashed arrows 43, 45, 48, which go not from left to right like the favored horizontal direction of travel SH, but from right to left.

It is thus possible by virtue of this to simulate the reverse saccade movements previously described while the individual 1 is reading a text. Indeed, here four times out of ten, the movement of the eyes 3 of the individual 1 following the target 20 of the gaze between two successive positions takes place in the direction opposite to the favored direction of travel.

Just as for the saccade movements detailed above, the target 20 may pass from one position to the following position, in a direction of travel opposite to the favored direction of travel, either by jumping from one position to the other (invisible target), or by moving from one to the other (visible target).

A method for determining at least one optical parameter for designing an ophthalmic lens intended to be mounted in a frame chosen by the individual, depending on the visual behavior thereof, this method using the testing device described above, will now be described with reference to FIGS. 4 to 18.

According to the invention, the determining method comprises the following steps:

a) the individual is asked to perform a visual task in which he looks at the target displayed by said display of the display device, the positions of said target being predetermined in a frame of reference attached to an image-capturing apparatus, b) images of the head of the individual looking at said target are captured by means of said image-capturing apparatus, each image corresponding to a predetermined position of said target, c) on the basis of at least some of the images of the head of the individual, positions of the head of the individual in a frame of reference attached to said image-capturing apparatus or gaze directions of the individual in a frame of reference attached to the head of the individual are determined, each position of the head or gaze direction of the individual being associated with the position of said target for which the corresponding image of the head of the individual was captured, d) said sought-after optical design parameter is deduced from said cephalic positions or gaze direction of the individual.

Figure 4:
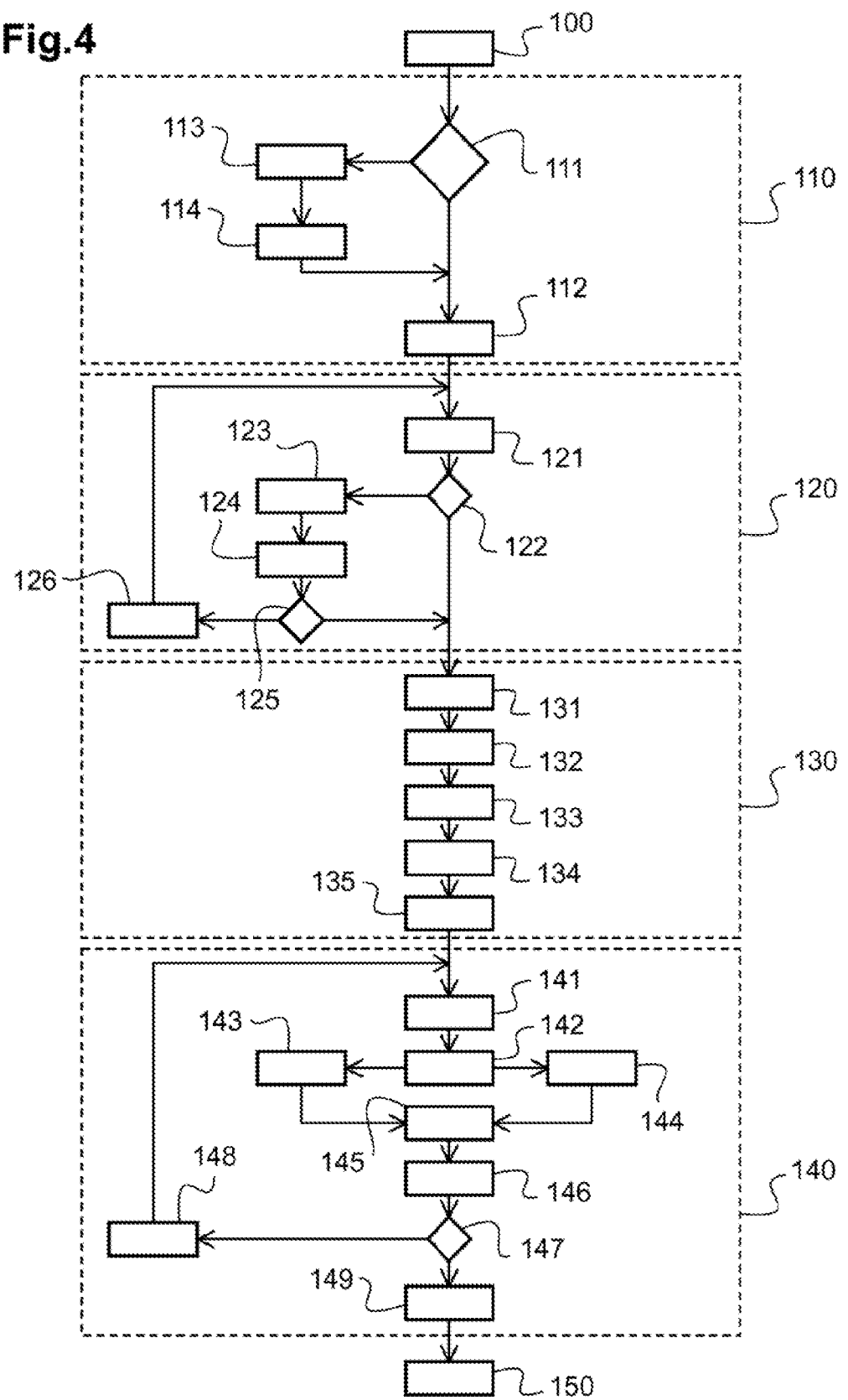
FIG. 4 shows a flowchart of a method for determining an optical design parameter using the device of FIG. 1.

FIG. 4 shows a flowchart of various steps that may advantageously be implemented in the determining method of the invention. These various steps may be grouped into six blocks 100, 110, 120, 130, 140 and 150 comprising one or more sub-blocks each representing one particular step.

In practice, the tablet 10, or a local or remote computer, is programmed to accomplish the steps described below.

Block 100

In an initial identifying step, represented by the block 100 of FIG. 4, the individual is asked to provide his name and surname. This step may be carried out by means of the tablet itself, for example by displaying on the screen 11 of the tablet 10 fields to be completed by the individual 10.

In this identifying step, the individual is also asked to select, depending on his reading characteristics or preferences, an initial writing system i.e. to specify the horizontal and vertical directions of travel that he would prefer: from left to right or right to left, and from top to bottom or bottom to top.

Lastly, a reading speed of the individual is stored in memory. This reading speed may be evaluated by asking the individual to indicate, for example by clicking on an icon displayed on the screen, whether his reading speed is slow, normal, or indeed fast. Depending on this reading speed, the predetermined display duration of the target will possibly be adjusted (see blocks 113 and 118 below).

As a variant, this reading speed could be evaluated on the basis of a reading of an actual text, of a length that is sufficient to ensure that this reading speed corresponds to the average speed with which the entire text is read. Advantageously, the read text may be used to determine the displayed positions of the visually predominant target of the visual tracking protocol (see below).

It is also possible to envisage doing a training run with an average speed, asking the individual if this average speed was too fast or not fast enough and adjusting the speed depending on his response.

All of these personal data may also be automatically imported from a database following transmission, to the database server, of the name and surname of the individual and optionally of other personal data such as age, address, etc.

Block 110

The purpose of the steps grouped together in block 110 of FIG. 4 is to construct a coordinate system attached to the head 4 of the individual 1, this system being called the "FV posture coordinate system" or the "frame of reference CRO". The head 4 of the individual 1 has a set orientation and position in this system and a coordinate system, preferably an orthonormal coordinate system, having an origin and three unrelated axes is associated therewith.

FIGS. 5 and 6 illustrate how this frame of reference CRO is constructed.

In particular, FIG. 5 shows a vertical plane PV corresponding to a sagittal plane of the head 4 of the individual 1, which is the vertical plane passing through a perpendicular bisector of the two eyes of the individual 1, i.e. the right eye OD and left eye OG.

This perpendicular bisector of the eyes OD, OG is an axis which passes through the middle of a segment which is defined by the center of rotation of the right eye OD (hereinafter referenced CROD) and the center of rotation of the left eye OG (hereinafter referenced CROG) and which is parallel to the Frankfurt plane of the head 4 of the individual 1.

The Frankfurt plane of the head of the individual is defined as the plane passing through the lower orbital points of the individual 1 and the portion of the individual 1, the portion being the auditory canal's highest point of the skull, which corresponds to the tragion of the ear. For the determination of the Frankfurt plane, it is considered that the individual is in an orthostatic position, in which he exerts minimum effort. This position corresponds to a natural posture, hereinafter designated "FV posture".

In this natural position, the gaze direction of the individual is then the primary gaze direction, that is to say that he gazes straight ahead. The Frankfurt plane is then generally horizontal.

Moreover, a horizontal plane PH that is, on the one hand, parallel to the Frankfurt plane of the head 4 of the individual 1 and, on the other hand, contains the centers of rotation CROD, CROG of the eyes OD, OG of the individual 1, is defined.

On the basis of the FV posture of the individual 1, that is to say of the knowledge of the orientation of the Frankfurt plane, and of the centers of rotation CROD, CROG of the eyes OD, OG of the individual 1, it is possible to construct the frame of reference CRO attached to the head 4 of the individual 1, hereinafter referenced $R_{CRO}$, by choosing:
- an origin which is one of the centers of rotation CROD, CROG of the right eye OD or of the left eye OG of the individual 1 or a centroid of these centers of rotation CROD, CROG;
- a first axis that passes through the origin and the right and left rotation centers CROD, CROG;
- a second axis that passes through the origin and that is parallel to the primary gaze direction of the individual 1; and
- a third axis that passes through the origin and that is perpendicular to the first and second axes (the third axis corresponds to the "vector product" of the second axis and first axis).

In the particular embodiment detailed here, the origin of the frame of reference $R_{CRO}$ is chosen as being the point situated in the middle of the segment joining the center of rotation CROD of the right eye OD and the center of rotation CROG of the left eye OG of the individual 1. In other words, this origin point, designated hereinafter "cyclops CRO" and referenced $CRO_C$ corresponds to the centroid of the centers of rotation CROD, CROG of the eyes OD, OG of the individual 1.

The three axes $X_H$, $Y_H$, $Z_H$, of the frame of reference $R_{CRO}$ are also shown in FIG. 6.

The axis $X_H$ (first axis) is oriented here from the left center of rotation CROG to the right center of rotation CROD. The axis $X_H$ is therefore contained in the horizontal plane PH parallel to the Frankfurt plane. An opposite orientation is also possible.

The axis $Z_H$ (second axis) is located in the vertical plane PV of the head 4 of the individual 1 and is parallel to the Frankfurt plane. It is therefore parallel to the primary gaze direction when the individual 1 is in a natural position, that is to say in the FV posture. The axis $Z_H$ extends here in a direction away from the head 4 of the individual 1 (towards the rear).

The axis $Y_H$ (third axis) extends, for its part, in the vertical sagittal plane PV of the head 4 of the individual 1 and is perpendicular to the Frankfurt plane. The axis $Y_H$ is therefore indeed perpendicular to the axis $X_H$ and to the axis $Z_H$. It is oriented upwards here, so that the frame of reference $R_{CRO}$ is right-handed. It will be noted that the frame of reference $R_{CRO}$ is attached to the head 4 of the individual 1 and that therefore this frame of reference $R_{CRO}$ shifts with the head 4 of the individual 1, the position and the orientation of this frame of reference $R_{CRO}$ changing, with respect to an absolute frame or a frame of reference not attached to the head 4 of the individual 1, depending on the movements of the head 4 of the individual 1.

As mentioned above, the block 110 is intended for construction of the frame of reference $R_{CRO}$ from data provided by the individual 1 or indeed from measurements carried out on the individual 1.

Thus, in a step represented by the sub-block 111, it is checked whether, for the individual 1 identified beforehand (see block 100), the positions of the centers of rotation CROD, CROG and the FV posture are available.

If these data are available, then a step of creating the FV-posture coordinate system such as described above and represented by the sub block 112 is passed to. The data may be available locally, i.e. recorded in a memory of the tablet 10, or indeed available remotely, i.e. be recorded in a database to which requests may be made with regard to importing said data.

If these data are not available, then it is necessary, on the one hand, to determine the respective positions of the centers of rotation CROD, CROG (sub-block 113) of the eyes OD, OG of the individual 1, and on the other hand to determine the FV posture (sub-block 114) of the individual 1.

The positions of the centers of rotation CROD, CROG may be determined according to a principle that is known per se and set forth for example in document FR 2914173, an equivalent of which in English is document US 2010/0128220.

In the step of determining the centers of rotation CROD, CROG (sub-block 113), the individual 1 wears, on his head 4, fastened to his head 4, a locating system (metrological coordinate system) or "clip" which comprises locating elements (markers) that are detectable during capture of an image of the head 4 of the individual 1.

To summarize, at least two images of the head 4 of the individual 1 are captured by means of an image-capturing apparatus:
 a first image when the individual gazes at the image-capturing apparatus while being positioned face-on, gazing straight ahead into the far distance (FV posture), and
 a second image when the individual gazes at the image-capturing apparatus while being positioned three-quarters-on.

If the tablet 10 is equipped with a rear video camera, the latter may advantageously serve as image-capturing apparatus. Otherwise, provision may be made for an image-capturing apparatus that is independent of the tablet.

On the basis of processing of the two captured images (see document FR 2914173), the positions of the centers of rotation CROD, CROG are deduced in a coordinate system attached to the locating system.

It is then possible to determine a particular point, designated below the "cyclops" center of rotation or "cyclops CRO" and referenced $CRO_C$, that is the isobaric center of the two centers of rotation CROD, CROG determined beforehand.

In the following step of determining FV posture, which step is represented by sub-block 114, the positions of the centers of rotation CROD, CROG and the face-on first captured image are used to determine the FV posture of the individual 1. Provision may also be made to compensate for the inclination of the tablet 10 during the latter determination (see for example documents U.S. Pat. Nos. 8,231,220 and 7,950,800).

Thus, at the end of the steps represented by the sub-blocks 113 and 114, data usable to create the FV-posture coordinate system are available and the creating step described above with reference to the sub-block 112 may be implemented.

Block 120

Next, in a set of steps represented by the block 120, adjustments are preferably made to the tablet 10 in order to allow the precision and reliability of the measurements of the position of the head 4 of the individual 1 or of the gaze directions of the individual 1 to be improved.

Thus, in a step represented by the sub-block 121 and illustrated in FIG. 7, the positions of the markers of the clip are determined in the field of the front video camera 13 of the tablet 10, with the front video camera 13 oriented upward.

To this end, an element, here a circle 23, is displayed at the center of the screen 11, and the individual 1, who is holding the tablet 10 in his hand, is asked to look at the circle 23.

As a variant, this element could be displayed in the first displayed position (see position 31 of FIG. 3) of the target.

In a following step (sub-block 122), the front video camera 13 of the tablet 10 is commanded to acquire images of the head 4 of the individual 1 equipped with the locating system used beforehand and, on the basis of processing of the acquired images, it is determined:
 i) whether the position of the markers of the clip has remained for a preset time in the upper two thirds of the field of the video camera 13;
 ii) whether the position of the markers of the clip has remained for a preset time in the bottom third of the field of the video camera 13; or iii) that the position of the markers of the clip was not determinable within a time limit.

In case i), it is then possible to continue to the step represented by the sub-block 131 of the training phase represented by the block 130.

In case iii) above, the method continues with the step represented by the sub-block 123, in which a figure, here a cross 24 (see FIG. 8), is displayed on the screen 11, this cross indicating to the individual 1 that a measurement error has been detected with respect to the field of the video camera 13.

Next in case iii), or indeed in case ii), a figure, here an arrow 25 with a circularly arcuate shape (see FIG. 9) is displayed on the screen 11, this figure indicating to the individual 1 to to flip the tablet 10 so as to place the front video camera 13 at the bottom.

Preferably, provision is made in this step to check that the tablet 10 has indeed been flipped by the individual 1 (see FIG. 10). Advantageously, this check may be carried out by virtue of sensors that are able to sense the orientation of the tablet 10, gyrometers for example.

Figure 11:
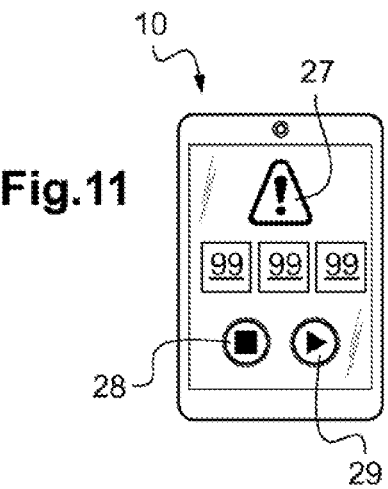
Figure 12:
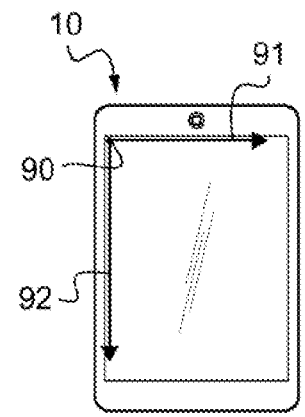
FIG. 12 illustrates a frame of reference attached to the testing device of FIG. 1.
Figure 13:
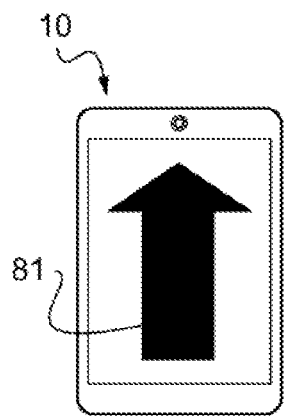
FIG. 13 shows the testing device of FIG. 1 in a training phase of the method of the invention.
Figure 14:
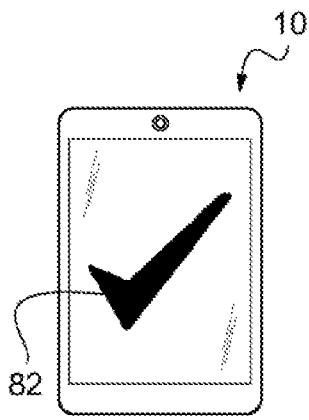
FIGS. 14 and 15 show the testing device in a verifying step of a measuring phase of the method of the invention.
Figure 15:
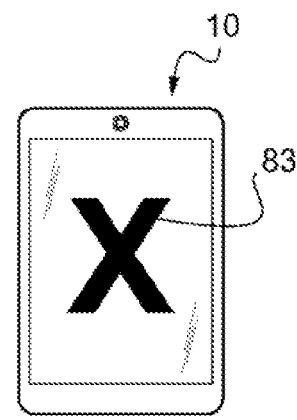

Once the check has been performed, the method passes to the step represented by the sub-block 124 and illustrated in FIG. 11, in which step the positions of the markers of the clip are determined in the field of the front video camera 13 of the tablet 10, with the front video camera 13 oriented downward.

An element, here a circle 26, is then displayed at the center of the screen 11, and the individual 1, who is holding the tablet 10 in his hand, is asked to look at this circle 26.

As a variant, this element could be displayed in the first displayed position (see position 31 of FIG. 3) of the target.

In a following step (sub-block 125), the front video camera 13 of the tablet 10 is commanded to acquire images of the head 4 of the individual 1 equipped with the locating system used beforehand and while he is holding the tablet in his hands 2.

On the basis of processing of the acquired images it is then determined:
 i) whether the position of the markers of the clip has remained for a preset time in the field of the video camera 13; or
 ii) that the position of the markers of the clip was not determinable within a time limit.

In case i), it is then possible to continue to the step represented by the sub-block 131 of the training phase represented by the block 130.

In case ii) above, the method continues with the step represented by the sub-block 126, in which a symbol 27 (see FIG. 11), is displayed on the screen 11, this symbol indicating to the individual 1 that the clip has not been detected or that a computing error has occurred.

The tablet 10 then displays a message and requests that the step in course be restarted (see button 29) or that the test be ended (see button 28).

In addition, pictograms (not shown but that would be located in the empty boxes 99 in FIG. 11) recalling the essentials of good practice are displayed.

For example, these pictograms may remind the individual 1:
  to pay attention to the presence of annoying lights that may be a source of glare (for example ceiling lights, large windows behind the back of the individual);
  to clear the field of vision of the front video camera 13, which could be obstructed by the finger of the hand or indeed of an item of clothing that he is wearing.

At the end of the steps of block 120 (adjusting phase), the front video camera 13 of the tablet 10 has been placed under conditions that are optimal with respect to allowing the individual 1 to take measurements without needing to adjust his posture or the tablet 10 during the visual tracking protocol.

Block 130

Preferably, steps 131, 132, 133, 134, 135 of the block 130, which corresponds to a training phase, are carried out before the actual measuring phase (steps of the block 140, see FIG. 4).

In a first step of the training phase, a training visual tracking protocol chosen at random from a set of accessible visual tracking protocols is either computed, or loaded into a memory provided for this purpose in the control unit.

This set of accessible visual tracking protocols is determined depending on the favored reading directions indicated by the individual in the initializing step (block 100, see above). This set may be directly available in a memory of the tablet 10 or indeed be downloaded from a remote server.

The visual tracking protocol includes data representative of the position of the visually predominant target 20 to be displayed on the screen 11 of the tablet 10.

These representative data comprise:
  an index (natural integer) of the position of the target 20;
  a display time coordinate of the target 20 identified and expressed in seconds with respect to the start of the visual tracking protocol;
  two coordinates of the displayed positions of the target 20 on the screen 11, these coordinates being expressed with respect to a screen frame of reference, referenced $R_{SCR}$ below, having as origin the upper left-hand corner 90 of the screen 11 (see FIG. 12) and comprising two axes 91, 92 that are perpendicular to each other and oriented along the columns and rows of the screen 11.

In other words, at each instant, the position of the target 20 is known in the screen frame of reference $R_{SCR}$ attached to the image-capturing apparatus 13.

Once the visual tracking protocol has been loaded, the target 20 is first displayed, on the screen 11 of the tablet 10, in the first position (index=0) of the visual tracking protocol, for a preset time (sub-block 132). Provision may be made for an audio indicator or a vibration of the tablet 10 to indicate the start of the visual tracking protocol.

Next (sub-block 133), depending on the training visual tracking protocol chosen, the visually predominant target 20 is displayed in its successive positions. The travel speed of the protocol may be adjusted depending on information provided in the initializing phase (block 100) regarding the reading speed of the individual 1.

In this step, the user 1 gets used to tracking with his gaze the visually predominant target 20 that sequentially adopts all of the predetermined displayed positions of the loaded training visual tracking protocol.

As explained above, the displayed positions of the target 20 are adapted to simulate the reading of a text by the individual 1. Thus, in the training phase (block 130), the user 1 will gradually adopt a posture corresponding to his natural posture in a pseudo-reading situation.

When the preceding step (sub-block 133) has ended, it is preferably possible to display on the screen 11 (see FIG. 13, sub-block 134) a figure indicating the end of the cycle. An audio indicator or a vibration may also indicate the end of the cycle.

In this step (sub-block 134), the displayed figure, here an upward-pointing arrow 81, represents an indicator inciting the individual to look off into the distance.

This FIG. 81 remains displayed on the screen 11 for a set time before disappearing. The tablet 10 then displays nothing on the screen 11 and awaits a set time.

After this wait, the state of advance of the learning phase is checked (sub-block 135). In particular, if the user has performed the visual tracking protocol only once, steps 133 and 134 are preferably restarted and carried out a second time. Otherwise, the first step (sub-block 141) of the actual measuring phase (block 140) is passed to.

Block 140

In this first step 141, which is similar to the first step 131 of the training phase (block 130), a measuring visual tracking protocol chosen at random from a set of accessible visual tracking protocols, which set is determined beforehand, is either computed, or loaded into a memory provided for this purpose in the control unit.

This visual tracking protocol includes similar data that are representative of the display position of the visually predominant target 20 on the screen 11 of the tablet 10 in the measuring phase.

These data in particular include the displayed positions of the visually predominant target 20, which are predetermined and known in the frame of reference $R_{SCR}$ attached to the image-capturing apparatus (front video camera 13) of the test device (tablet 10).

Figure 16:
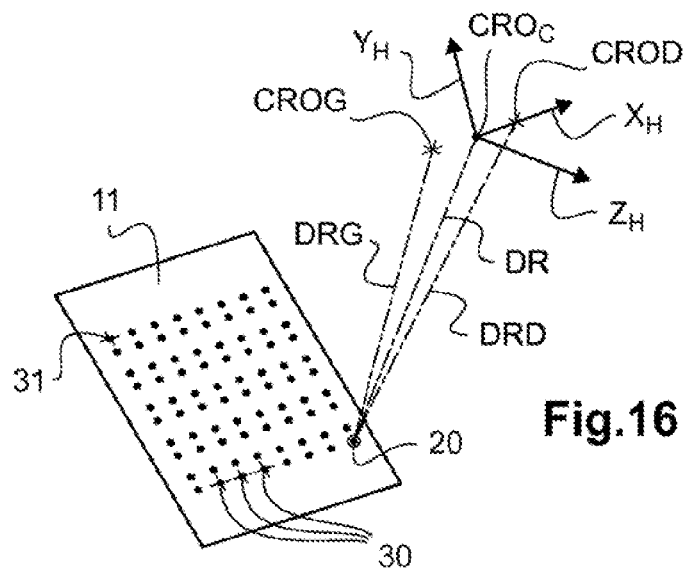
FIG. 16 shows the display of the testing device with targets displayed and a frame of reference attached to the head of the individual looking at the target in a final position of the protocol.

In a step a) of the determining method according to the invention, which is represented by sub-blocks 142 and 143 of FIG. 4, the individual 1 is asked to carry out a visual task in which he looks at the target 20 displayed by the screen 11 of the tablet 10 (see FIG. 16). The displayed positions 30 of this target 20 are predetermined in the frame of reference $R_{SCR}$ (cf. origin 90 and axes 91, 92 of FIG. 3) attached to the front video camera 13.

More precisely, the target 20 is first displayed (sub-block 142), on the screen 11 of the tablet 10, in the first position 31 (index=0) of the visual tracking protocol loaded for the measurement, for a preset time.

Provision may also be made for an audio indicator or a vibration of the tablet 10 to indicate the start of the visual tracking protocol.

Next (sub-block 143), depending on the measuring visual tracking protocol, the visually predominant target 20 is displayed in its successive positions 30. The travel speed of the protocol may be adjusted depending on information provided in the initializing phase (block 100) regarding the reading speed of the individual 1.

In this step a), the user follows with his gaze the visually predominant target 20, which sequentially adopts all of the predetermined displayed positions 30 of the loaded visual tracking protocol (see FIG. 16, in which the target 20 is displayed in the last position of the visual tracking protocol).

In step b) of the determining method, which is represented by the sub-block 144, images of the head 4 of the individual 1 looking at the target 20, which moves over the screen 11 according to the loaded visual tracking protocol, are captured by means of the front video camera 13 of the tablet 10, which is turned toward the head 4 of the individual 1.

Advantageously, the front video camera 13 triggers an image capture of the head 4 of the individual 1 with a capture offset with respect to the moment at which the target 20 is displayed at the predetermined positions 20 of the visual tracking protocol on the screen 11. This offset can be zero, or else preferably small, for example less than 200 milliseconds. This makes it possible to take into account the reaction time and displacement time of the eyes 3 of the individual 1 during a change of position 30 of the target 20 on the screen 11.

According to a variant, the front video camera can also carry out a continuous video sequence, for example at a rate of twenty images per second, and extract from the video sequence the best image giving the best information on the visual behavior of the individual during the display of the target at the corresponding target position.

Each image captured by the front video camera 13 of the tablet 10 thus corresponds to a predetermined position of the visually predominant target 20, whose position 30 in the frame of reference $R_{SCR}$ attached to the image-capturing apparatus 13 is known perfectly (see sub-block 141 above and FIG. 16).

Then, in step c) of the determining method according to the invention, on the basis of at least some of the images of the head 4 of the individual 1, either the positions of the head 4 of the individual 1 in the coordinate system $R_{SCR}$ attached to the front video camera 13, or the gaze directions of the individual 1 in the frame of reference $R_{CRO}$ attached to the head 4 of the individual 1 are determined, each position of the head 4 or gaze direction of the individual 1 being associated with the position 30 of the target 20 for which the corresponding image of the head 4 of the individual 1 was captured.

To this end, provision is made for the tablet 10 to comprise image processing means, for example consisting of the processor of the tablet 10, which detect, in the captured images of the head is 4 of the individual 1, the markers of the clip worn by the individual 1 on his head 4.

The position and the orientation of the clip in the frame of reference $R_{SCR}$ attached to the front video camera 13 are then determined for each captured image, that is to say for each position 30 of the target 20 of the visual tracking protocol, for example by using the method described in document FR 2914173 (an equivalent of which in English is the document U.S. Pat. No. 8,360,580).

Since the positions of the centers of rotation CROD, CROG of the eyes of the individual 1 with respect to the clip are known (see sub-blocks 111 and 114), the position (spatial coordinates) and the orientation (angular coordinates) of the frame of reference $R_{CRO}$ attached to the head 4 of the individual 1 are also known with respect to the clip.

This is moreover illustrated in FIG. 16 in which the frame of reference $R_{CRO}$ has been shown with its origin at the cyclops center of rotation $CRO_C$ (centroid of the centers of rotation CROD, CROG) and its axes $X_H$, $Y_H$, $Z_H$.

Thus, through a change of frame of reference, it is possible to determine, for each position 30 of the target 20 of the visual tracking protocol, the position and the orientation of the head 4 of the individual 1 in the frame of reference $R_{SCR}$ attached to the front video camera 13 of the tablet 10.

It is also possible to determine, for each position 30 of the target 20 of the visual tracking protocol, the gaze directions DR of the individual 1 in the coordinate system $R_{CRO}$ attached to the head 4 of the individual 1, these gaze directions DR here joining the cyclops center of rotation $CRO_C$, origin of the frame of reference $R_{CRO}$ attached to the head 4 of the individual 1, to the target 20.

It is also possible to determine the gaze directions DRD, DRG (see FIG. 16) relative to the right center of rotation CROD and to the left center of rotation CROG, respectively.

In one preferred embodiment, prior to step d), on the basis of the positions and orientations of the head 4 or of the gaze directions DR of the individual 1, the positions 70 of the target 20 are then re-expressed in the frame of reference $R_{CRO}$ attached to the head 4 of the individual 1.

Figure 17:
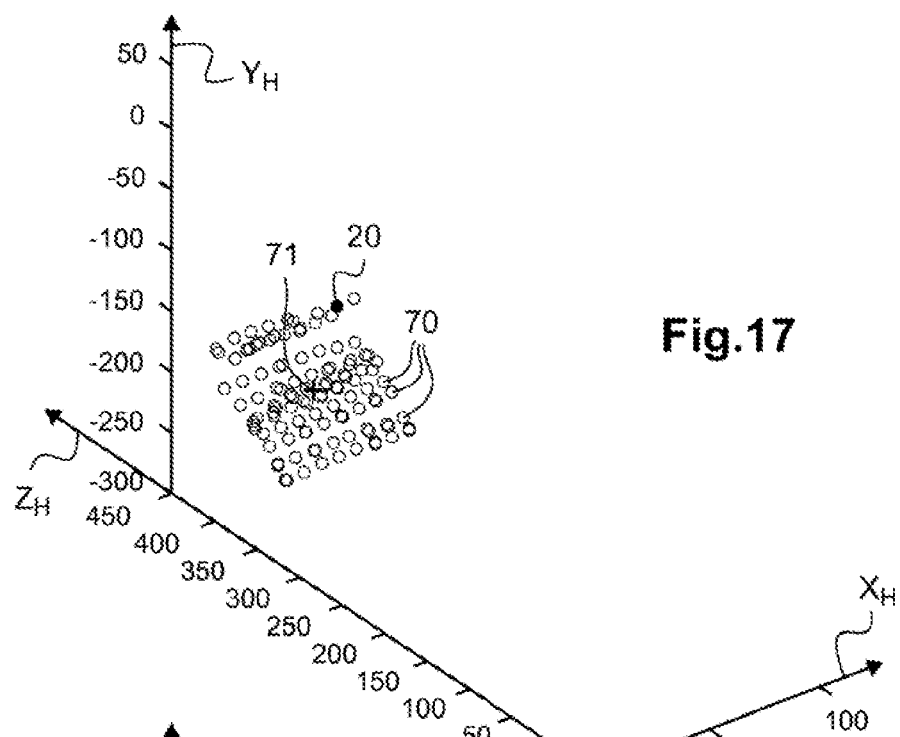
FIGS. 17 and 18 show examples of measured positions of the target in the coordinate system attached to the head of the individual over the course of the reading protocol.
Figure 18:
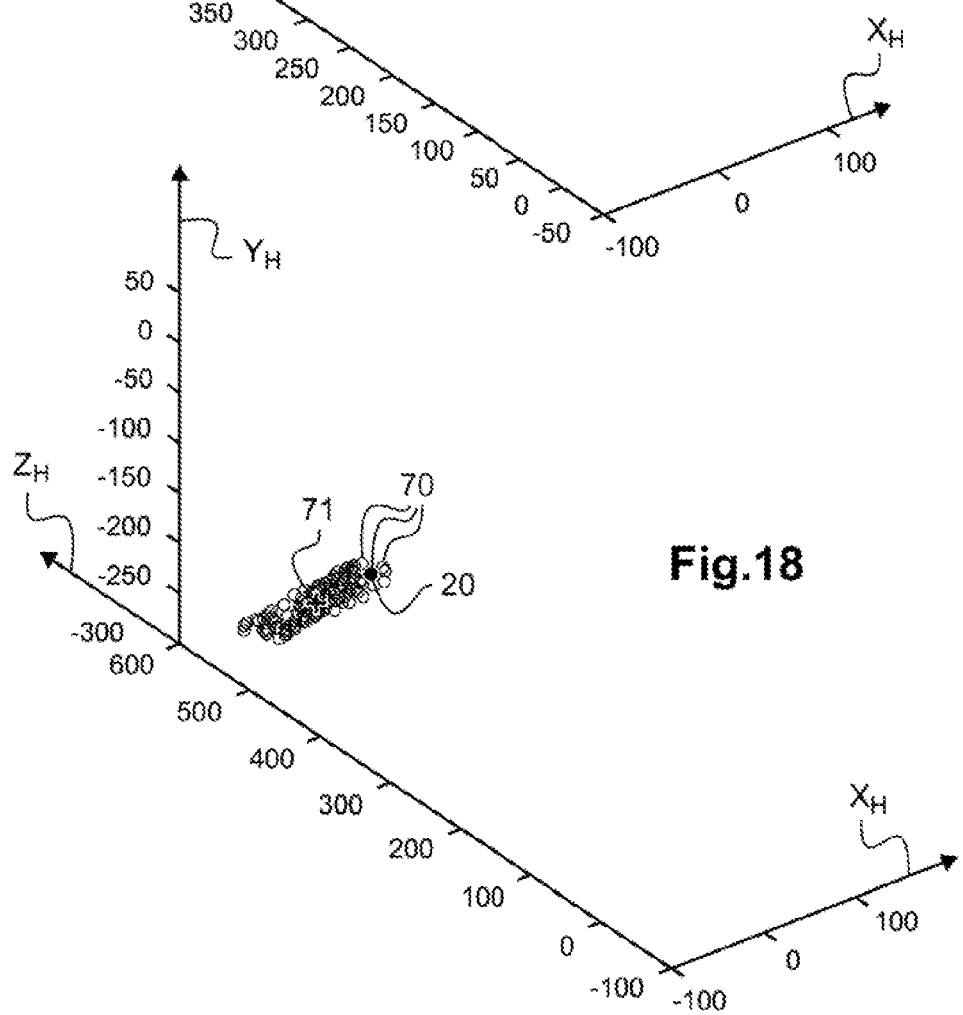

This is illustrated in FIG. 17 in which the positions 70 of the target 20 in this frame of reference $R_{CRO}$ have been shown with respect to the axes $X_H$, $Y_H$, $Z_H$ of the frame of reference $R_{CRO}$ attached to the head 4 of the individual 1.

On account of the fact that not only does the position and the orientation of the head 4 of the individual 1 change, during the eye test protocol, with respect to the frame of reference $R_{SCR}$ attached to the image-capturing apparatus 13, but that the individual 1 also modifies the position and the orientation of the tablet 10 during the eye test, it will be understood that the relative positions 70 of the target 20 in the frame of reference $R_{CRO}$ attached to the head 4 of the individual 1 provide information on the visual behavior of the individual 1, and in particular on his propensity to move his head 4 or eyes 3 while reading a text.

Specifically, if the individual 1 follows the visual tracking protocol while greatly modifying his gaze direction DR, then the relative positions 70 of the target 20 in the frame of reference $R_{CRO}$ attached to the head 4 of the individual 1 are similar to the relative positions 30 of the target 20 in the frame of reference $R_{SCR}$ attached to the front video camera 13. This is the case in FIG. 17.

Conversely, if the individual 1 follows the visual tracking protocol while maintaining an almost stationary gaze direction DR, then the positions 70 of the target 20 in the frame of reference $R_{CRO}$ attached to the head 4 of the individual 1 are grouped together. This is the case in FIG. 18.

Moreover, it is possible to associate with these positions 70 of the target 20 in the frame of reference $R_{CRO}$ associated with the head 4 of the individual 1 an index and a time coordinate such as described above with respect to the sub-block 141.

In a step d) of the determining method, which is here represented by the sub-block 146, the sought-after optical design parameter is deduced from the positions of the head 4 of the individual or from the gaze direction DR of the individual.

In the described particular embodiment, the sought-after optical design parameter is here deduced from the positions 70 of the target 20 in the frame of reference $R_{CRO}$ attached to the head 4 of the individual 1.

This optical design parameter may for example comprise the datum of the coordinates of the centroid 71 of the positions 70 of the target 20 in the frame of reference $R_{CRO}$ attached to the head 4 of the individual 1. This centroid 71 defines an average gaze direction of the individual 1, which joins the cyclops center of rotation $CRO_C$ and said centroid 71.

This average gaze direction is representative of the near-vision visual behavior of the individual 1 in a reading situation.

The datum of the coordinates of the centroid 71 in the frame of reference $R_{CRO}$ attached to the head 4 of the individual 1 may therefore be used to design an ophthalmic lens, in particular a progressive ophthalmic lens, intended to be mounted in a spectacle frame chosen by the individual 1.

As is described in document FR 3012952, it is for example possible, on the basis of knowledge of the centroid 71 and the average gaze direction, to precisely position a near-vision reference point (NV centering point) on an ophthalmic lens and also to optimize the design of the front and back surfaces of the ophthalmic lens in order to better tailor the latter to the individual 1.

By virtue of the positions 70 of the target 20 in the frame of reference $R_{CRO}$ attached to the head 4 of the individual 1, it is also possible to deduce an optical design parameter that takes into account the tendency of the individual 1 to move his head 4 and/or his eyes 3 during a reading task.

As mentioned above with reference to FIGS. 19 and 20, this optical design parameter may correspond to a datum representative of the dispersion of the positions 70 of the target 20 in the frame of reference $R_{CRO}$ attached to the head 4 of the individual 1.

This dispersion may be determined by calculating, for each position 70, the distance between this position 70 and the position of the previously defined centroid 71.

Since the positions 30 of the target 20 are here distributed both horizontally and vertically, a horizontal dispersion coefficient and a vertical dispersion coefficient may also be determined. The horizontal dispersion coefficient quantifies the movements of the eyes 3 of the individual 1 from left to right (or right to left) during the visual tracking protocol. The vertical dispersion coefficient for its part quantifies the movements of the eyes 3 of the individual 1 from top to bottom (or bottom to top) during the visual tracking protocol.

Other optical design parameters representative of the visual behavior of the individual may of course be determined.

In a following step, here represented by the sub-block 147, it is verified that the optical design parameter was determined with success.

For example, when this optical design parameter comprises the datum of the coordinates of the centroid 71 (see FIG. 17) of the positions 70 of the target in the frame of reference attached to the head 4 of the individual 1, it may be verified that the coordinates of this centroid 71 are comprised in specific ranges that are dependent on the positions 30 of the target 20 in the frame of reference $R_{SCR}$ of the tablet and on minimum and/or maximum amplitudes of the movement of the head 4 of the individual 1.

Any determined value outside of these limits causes an error to be generated. Two cases are then possible:
- if it is the first time that the measurement has been carried out, then the error is maintained and an error signal (here a cross 83, see FIG. 15) is displayed on the screen 11 of the tablet 10 (sub-block 148, see also sub-block 126);
- if it is the second measurement and if an error is signaled then the error is canceled and all the values are set to the minimum limit. This case will be detected as an aberrant value and will be managed accordingly.

In the case where the preceding verification goes okay, a symbol indicating success (see the V-shaped symbol 82 in FIG. 14) is displayed on the screen and the method passes to the following step, which is represented by the sub-block 149 and which consists in encoding the various deduced optical design parameters into a determined format.

It is for example possible to encode each of the coordinates of the centroid 71 of the positions 70 of the target 20 in the frame of reference $R_{CRO}$ attached to the head 4 of the individual 1 in hexadecimal, in one or more bytes and preferably two bytes.

Block 150

In a transferring phase (block 150), the optical design parameters are transmitted to a local or remote processor intended to use said parameters with a view to optical design of an ophthalmic lens that is intended for the individual 1 and that is particularly well suited to his visual behavior, here his reading behavior in near vision.

The invention claimed is:

1. A device for testing visual behavior of an individual, comprising:
    an active display configured to display at least one visually predominant target in a plurality of positions that vary over time and that are aligned in at least one row or one column; and
    circuitry configured to control the display so that successively displayed positions of the target follow, over time, a visual tracking protocol,
    wherein the visually predominant target is designed to catch the eye of the individual following said target over the course of an eye test,
    wherein said visual tracking protocol corresponds to succession, over time, of positions adopted by the visually predominant target, and
    wherein the circuitry is further configured to impose, by the target, said visual tracking protocol on the individual successively looking in a plurality of particular desired directions that are each associated with a particular displayed position adopted by the target.

2. The testing device as claimed in claim 1, wherein all the successively displayed positions are such that the target remains in the visual field of the individual.

3. The testing device as claimed in claim 1, wherein positions of the target are aligned in at least two rows or two columns that are substantially parallel.

4. The testing device as claimed in claim 1, wherein the plurality of positions comprise, in each row or column, at least three aligned positions of the target.

5. The testing device as claimed in claim 1, wherein the controlling unit controls so that, in each position of the visual tracking protocol, the target is displayed for a predetermined duration.

6. The testing device as claimed in claim 5, wherein the predetermined duration is between 50 milliseconds and 1 second.

7. The testing device as claimed in claim 5, wherein the target remains stationary for the predetermined duration.

8. The testing device as claimed in claim 1, wherein the controlling unit controls so that there is a predetermined lag between the display of the target in two successive positions of the visual tracking protocol.

9. The testing device as claimed in claim 5, wherein the predetermined lag varies over a course of the visual tracking protocol.

10. The testing device as claimed in claim 8, wherein the target is invisible during the predetermined lag.

11. The testing device as claimed in claim 8, wherein the target is visible during the predetermined lag and moves between the two corresponding successive positions of the visual tracking protocol, from one to the other.

12. The testing device as claimed in claim 1, wherein the controlling unit controls so that two successive positions of the visual tracking protocol are separated by a distance smaller than 10 centimeters.

13. The testing device as claimed in claim 1, wherein the controlling unit controls so that two successive positions of the visual tracking protocol are separated by a distance that varies throughout the visual tracking protocol.

14. The testing device as claimed in claim 1, wherein the controlling unit stores a favored vertical direction of travel and a favored horizontal direction of travel of the visual tracking protocol in memory.

15. The testing device as claimed in claim 14, wherein the display of the target in two successive positions of the visual tracking protocol follows the favored direction of travel at least six times in ten.

16. The testing device as claimed in claim 14, wherein the positions of the target are aligned in at least two rows or two columns that are substantially parallel; and wherein the substantially parallel rows along which the predetermined positions of the target are aligned extending substantially horizontally, the direction of travel of the visual tracking protocol is identical for all the successive rows, from the highest to the lowest, from right to left or left to right.

17. The testing device as claimed in claim 14, wherein the positions of the target are aligned in at least two rows or two columns that are substantially parallel; and wherein the substantially parallel columns along which the predetermined positions of the target are aligned extending substantially vertically, the direction of travel of the visual tracking protocol is identical, from the top to bottom or bottom to top, for all the successive columns from left to right or right to left.

18. The testing device as claimed in claim 1, wherein the controlling unit is programmed to allow the visual tracking protocol to be selected from a plurality of visual tracking protocols recorded in a local or remote database in which a direction of travel is recorded in association with the visual tracking protocol to which it corresponds.

19. The testing device as claimed in claim 1, wherein the visual tracking protocol follows a reading trajectory which accords with that defined by a given writing system, to reproduce displacement of a gaze of the individual while reading in accordance with the writing system.

20. A method for determining at least one optical parameter for designing an ophthalmic lens mountable in a frame for an individual, depending on visual behavior of the individual, the method using a testing device for testing visual behavior of the individual, including an active display configured to display at least one visually predominant target in a plurality of positions that vary over time and that are aligned in at least one row or one column, and circuitry configured to control the display so that successively displayed positions of the target follow, over time, a visual tracking protocol, wherein the visually predominant target is designed to catch the eye of the individual following said target over the course of an eye test, wherein said visual tracking protocol corresponds to succession, over time, of positions adopted by the visually predominant target, and wherein the circuitry is further configured to impose, by the target, said visual tracking protocol on the individual successively looking in a plurality of particular desired directions that are each associated with a particular displayed position adopted by the target and comprising:

a) instructing the individual to perform a visual task in which the individual looks at the target displayed by the display of the display device, positions of the target being predetermined in a frame of reference attached to an image-capturing apparatus;

b) capturing images of the head of the individual looking at the target by the image-capturing apparatus, each image corresponding to a predetermined position of the target;

c) determining, on the basis of at least some of the images of the head of the individual, positions of the head of the individual in a frame of reference attached to the image-capturing apparatus or gaze directions of the individual in a frame of reference attached to the head of the individual, each position of the head or gaze direction of the individual being associated with the position of the target for which the corresponding image of the head of the individual was captured; and d) determining an optical design parameter from the cephalic positions or gaze direction of the individual.

21. The determining method as claimed in claim 20, further comprising, prior to d), re-expressing the positions of the target, on the basis of the determined positions of the head or the gaze directions of the individual, in a frame of reference attached to the head of the individual, and in d), deducing the sought-after optical design parameter from the positions of the target in the frame of reference attached to the head of the individual.

* * * * *